(12) United States Patent
Zhang et al.

(10) Patent No.: US 10,022,156 B2
(45) Date of Patent: Jul. 17, 2018

(54) MINIMALLY INVASIVE SCREW WITH DOUBLE THREADED PLUGS

(71) Applicants: Beijing Fule Science & Technology Development Co., Ltd., Beijing (CN); Huanyu Hu, Beijing (CN)

(72) Inventors: Wenzhi Zhang, Beijing (CN); Xiyi Huang, Beijing (CN); Guoshuai Miu, Beijing (CN); Yaling Wang, Beijing (CN); Wensheng Lu, Beijing (CN); Hongyan Li, Beijing (CN)

(73) Assignees: Beijing Fule Science & Technology Development Co., Ltd., Beijing (CN); Huanyu Hu, Beijing (CN)

( * ) Notice: Subject to any disclaimer, the term of this patent is extended or adjusted under 35 U.S.C. 154(b) by 0 days.

(21) Appl. No.: 15/509,559

(22) PCT Filed: Sep. 3, 2016

(86) PCT No.: PCT/CN2016/097978
§ 371 (c)(1),
(2) Date: Mar. 8, 2017

(87) PCT Pub. No.: WO2017/071403
PCT Pub. Date: May 4, 2017

(65) Prior Publication Data
US 2017/0290607 A1 Oct. 12, 2017

(30) Foreign Application Priority Data
Oct. 30, 2015 (CN) .......................... 2015 1 0727012

(51) Int. Cl.
*A61B 17/70* (2006.01)
*A61B 17/86* (2006.01)

(52) U.S. Cl.
CPC ...... *A61B 17/7032* (2013.01); *A61B 17/7049* (2013.01); *A61B 17/8605* (2013.01)

(58) Field of Classification Search
CPC ............ A61B 17/7032; A61B 17/7049; A61B 17/8605
(Continued)

(56) References Cited

U.S. PATENT DOCUMENTS 7,261,714 B2 * 8/2007 Richelsoph ........ A61B 17/7032
606/279
8,512,382 B2 * 8/2013 Cawley .............. A61B 17/7035
606/265
(Continued)

FOREIGN PATENT DOCUMENTS

CN 1931106 A 3/2007
CN 202376217 U 8/2012
(Continued)

OTHER PUBLICATIONS

Chinese Patent and Trademark Office, International Search Report and Written Opinion in corresponding PCT/CN2016/097978, dated Sep. 3, 2016 (13 pages).

*Primary Examiner* — Pedro Philogene
*Assistant Examiner* — David C Comstock
(74) *Attorney, Agent, or Firm* — Wood Herron & Evans LLP

(57) ABSTRACT

A minimally invasive screw with double threaded plugs is provided, for connecting to a connecting rod. The screw includes an inner threaded plug, an outer threaded plug, a lengthened arm connector, a press block and a pin with a hollow ball head. The connecting rod can be fixed to the lengthened arm connector via the press block, the inner and outer threaded plugs, to prevent the vertebral body from
(Continued)

rotating and loss of intervertebral height when the vertebral body is distracted and pressurized.

10 Claims, 5 Drawing Sheets

(58) Field of Classification Search
USPC ........ 606/264–270, 304, 308, 323; 403/362; 411/393
See application file for complete search history.

(56) References Cited

U.S. PATENT DOCUMENTS

| | | |
|---|---|---|
| 8,784,455 B2 | 7/2014 | Matthis et al. |
| 9,333,010 B2 | 5/2016 | Matthis et al. |
| 2002/0143341 A1 | 10/2002 | Biedermann et al. |
| 2003/0149431 A1* | 8/2003 | Varieur ............ A61B 17/7032 606/270 |
| 2006/0083603 A1* | 4/2006 | Jackson ............ A61B 17/7032 411/386 |
| 2006/0149235 A1* | 7/2006 | Jackson ............ A61B 17/7032 606/328 |
| 2014/0214084 A1* | 7/2014 | Jackson ............ A61B 17/7037 606/270 |
| 2014/0277153 A1* | 9/2014 | Spratt ............... A61B 17/7035 606/266 |
| 2015/0012042 A1 | 1/2015 | Black |

FOREIGN PATENT DOCUMENTS

| | | |
|---|---|---|
| CN | 102670294 A | 9/2012 |
| CN | 202821566 U | 3/2013 |
| CN | 204520926 U | 8/2015 |
| CN | 105213009 A | 1/2016 |
| CN | 205215336 U | 5/2016 |

* cited by examiner

MINIMALLY INVASIVE SCREW WITH DOUBLE THREADED PLUGS

CROSS-REFERENCE TO RELATED APPLICATIONS

This application is a national phase of PCT/CN2016/097978, filed on Sep. 3, 2016, which claims priority to Chinese Application No. 201510727012.9, which was filed Oct. 30, 2015. These prior applications are incorporated herein by reference, in their entireties.

TECHNICAL FIELD

The present invention relates to the technical field of medical instruments, in particular to a minimally invasive screw with double threaded plugs.

BACKGROUND

Surgery getting minimally invasive, functional and intelligent is a symbol of modern surgical techniques, and is also the future direction of the surgical techniques. Minimally invasive spinal surgical techniques combine traditional spinal surgery and minimally invasive techniques so as to reduce trauma to patients, alleviate post operation pain and sense of discomfort of patients, shorten time in bed and hospital stays, speed functional recovery of patients after operation, try to maintain the integrity of the normal anatomical structure of the spine and thus achieve the highest goal of, after operation, keeping the normal physiological function of the spine. However, the minimally invasive spinal surgery not only needs assistance and support of advanced instruments, but also requires operators to own very high tactile sensitivity, spatial discrimination capability and skilled operation capability via narrow work pipes. Especially important nerves, blood vessels and viscera in front of and adjacent to the spine bring great difficulties and challenges to the anterior spinal minimally invasive surgery.

Minimally invasive surgeries of percutaneous pedicle screw fixation and percutaneous channel operation largely avoid the detachment of paraspinal muscles, reduce the surgical trauma, and have a wide range of application, such as treatment for lumbar disc herniation or prolapse of lumbar intervertebral disc, lumbar spinal stenosis and scoliosis. Operative field for the percutaneous channel operation is wider than that for micro endo disc system, and the percutaneous channel operation may thus utilize conventional surgical instruments which are easy for doctors to operate. The percutaneous pedicle screw fixation is operated and finished under the guidance of fluoroscopy during operation. However, the common screw with threaded plug may cause vertebral body to rotate and loss of intervertebral height when the vertebral body is distracted and pressurized.

SUMMARY

To overcome the above mentioned disadvantages of the prior art, the present invention provides a minimally invasive screw with double threaded plugs which is capable of preventing the vertebral body from rotating when being distracted and pressurized.

To achieve the objective above, the invention provides a minimally invasive screw with double threaded plugs, connecting to a connecting rod, comprising an inner threaded plug, an outer threaded plug, a lengthened arm connector, a press block and a pin with a hollow ball head, wherein, the lengthened arm connector has a hollow interior, the connecting rod is configured to pass transversely through the lengthened arm connector, the outer threaded plug is movably disposed inside the lengthened arm connector, the inner threaded plug is movably disposed inside the outer threaded plug and is able to make the connecting rod be fixed on the lengthened arm connector, and the press block is disposed on the inner wall of the lengthened arm connector to make the pin be fixed to the end of the lengthened arm connector.

Preferably, the lower part of the inner threaded plug has a protrusion for engaging with the connecting rod.

Preferably, the upper part of the inner threaded plug is provided with a mounting groove for withstanding an external force to make the inner threaded plug rotate inside the outer threaded plug.

Preferably, the mounting groove is a hexagon socket.

Preferably, the outer threaded plug is provided with at least one opening.

Preferably, at least one pair of a first positioning groove is symmetrically arranged on the outer wall of the lengthened arm connector, the press block is provided with a second positioning groove, the second positioning groove and the first positioning groove are co-axially arranged such that the pin can be fixed to the end of the lengthened arm connector when an external force is applied and the first positioning groove and the second positioning groove are thus passed through.

Preferably, the outer wall or the inner wall of the lengthened arm connector is configured to have a groove for breaking the lengthened arm connector off in surgery.

Preferably, the outer wall and the inner wall of the lengthened arm connector are configured to have grooves, which are co-axially arranged, for breaking the lengthened arm connector off in surgery.

Preferably, the groove is disposed on the middle-upper part of the internal thread of the lengthened arm connector.

Preferably, the interior of the pin with a hollow ball head has a through hole.

The minimally invasive screw with double threaded plugs of the invention is provided with the press block, via which the pin is connected to the end of the lengthened arm connector to make the pin be locked within the range of motion. The connecting rod is fixed on the lengthened arm connector via the inner and outer threaded plugs to prevent the vertebral body from rotating and loss of intervertebral height when the vertebral body is distracted and pressurized and to ensure reliability of surgery.

DETAILED DESCRIPTION

To further describe the invention, the minimally invasive screw with double threaded plugs of the present invention will be described in detail in connection with embodiments, which should not be construed as limiting the scope of the invention.

Figure 1:
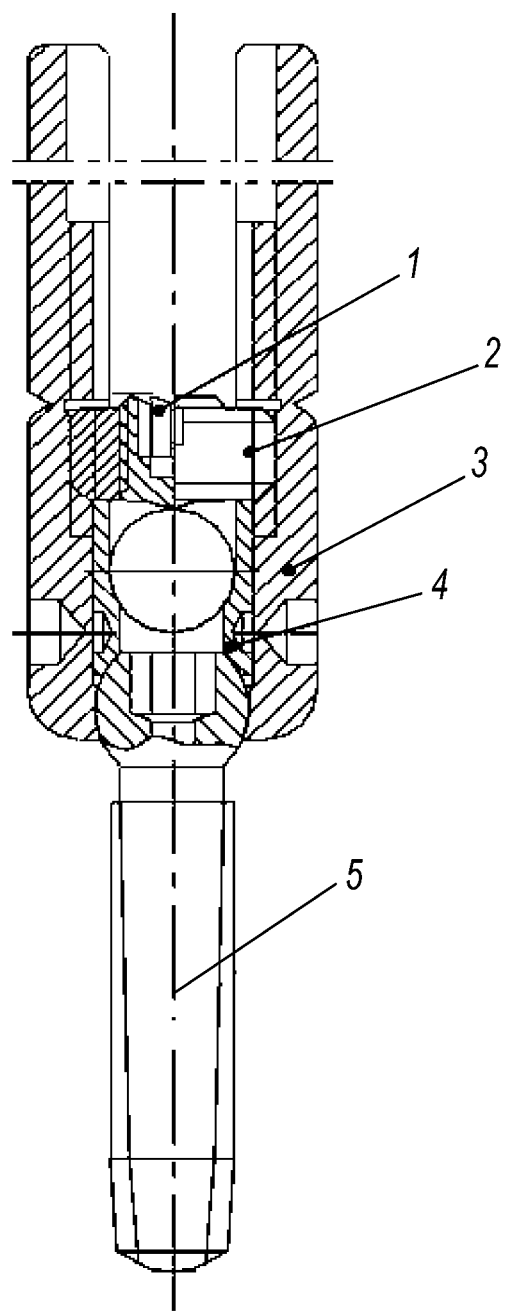
FIG. 1 is a schematic view of a minimally invasive screw with double threaded plugs of the present invention.

As shown in FIG. 1, a minimally invasive screw with double threaded plugs of the present invention is configured to be connected to a connecting rod 17. The minimally invasive screw with double threaded plugs of the invention is provided with an inner threaded plug 1, an outer threaded plug 2, a lengthened arm connector 3, a press block 4 and a pin 5 with a hollow ball head. The lengthened arm connector 3 has a hollow interior. The connecting rod 17 is configured to pass transversely through the lengthened arm connector 3. The outer threaded plug 2 is movably disposed inside the lengthened arm connector 3. The inner threaded plug 1 is movably disposed inside the outer threaded plug 2, and is able to make the connecting rod 17 be fixed on the lengthened arm connector 3. The press block 4 is disposed on the inner wall of the lengthened arm connector 3 to make the pin 5 be fixed to the end of the lengthened arm connector 3.

The minimally invasive screw with double threaded plugs of the invention is provided with the press block, via which the pin is connected to the end of the lengthened arm connector to make the pin be locked within the range of motion. The connecting rod is fixed on the lengthened arm connector via the inner and outer threaded plugs to prevent the vertebral body from rotating and loss of intervertebral height when the vertebral body is distracted and pressurized and to ensure reliability of surgery.

Figure 2:
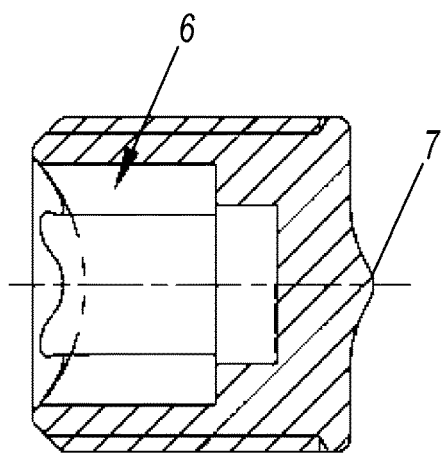
FIG. 2 is a front view of an inner threaded plug of the present invention.

As shown in FIG. 2, the lower part of the inner threaded plug 1 has a protrusion 7 for engaging with the connecting rod 17. By the inner threaded plug 1 being rotated inside the outer threaded plug 2 and being tightened, the connecting rod 17 can be finally locked. Furthermore, the degree of engagement can also be adjusted as needed. By virtue of the protrusion, the counter force against the relative movement between the pin and the connecting rod can be increased, such that the counter force against the rotation about the rod can be much higher, which is adaptable to the mechanical condition under which the rod is bent, a stable triangular mechanical structure thus being formed.

Figure 3:
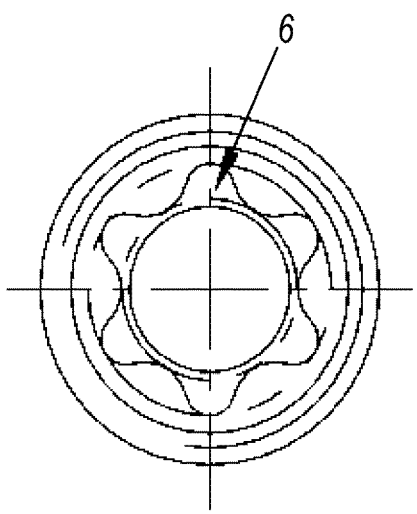
FIG. 3 is a top view of the inner threaded plug.

The interior of the lengthened arm connector 3 is provided with an internal thread 9. The outer threaded plug 2 is movably connected to the lengthened arm connector 3 via the internal thread 9. The outer wall of the inner threaded plug 1 is provided with an external thread. A threaded hole, that matches the inner threaded plug 1, is provided in the outer threaded plug 2. In order to facilitate mounting of the inner threaded plug 1 into the outer threaded plug 2, the upper part of the inner threaded plug 1 is provided with a mounting groove 6 (as shown in FIGS. 2 and 3) for withstanding an external force to make the inner threaded plug 1 rotate within the outer threaded plug 2. In this embodiment, the mounting groove 6 may be, but not limited to, a hexagon socket, and may also be, such as, an internal hexagon socket or cross-shaped groove.

Figure 4:
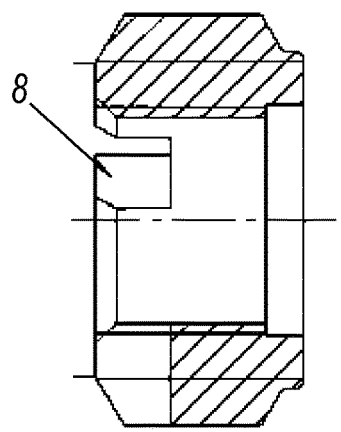
FIG. 4 is a front view of an outer threaded plug of the present invention.
Figure 5:
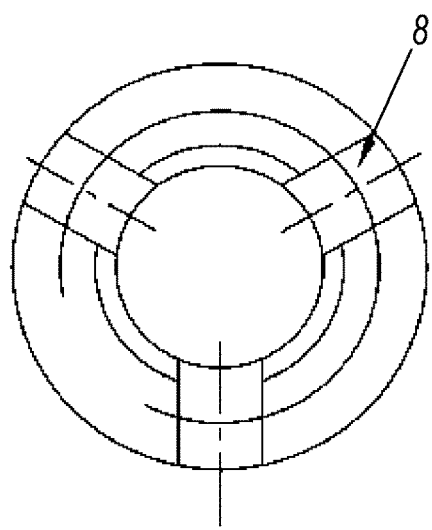
FIG. 5 is a top view of the outer threaded plug.

As shown in figures, the outer threaded plug 2 is provided with at least one opening (as shown in FIGS. 4 and 5) for withstanding an external force to cause the outer threaded plug 2 to rotate within the lengthened arm connector 3. In this embodiment, three such openings are provided such that forces applied on the outer threaded plug 2 can be uniform while the inner threaded plug 1 is rotating within the outer threaded plug 2.

Figure 6:
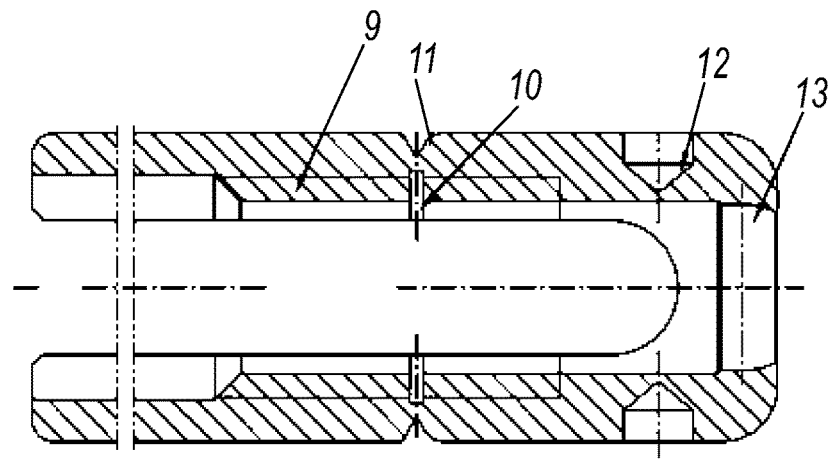
FIG. 6 is a schematic view of a lengthened arm connector of the present invention.
Figure 7:
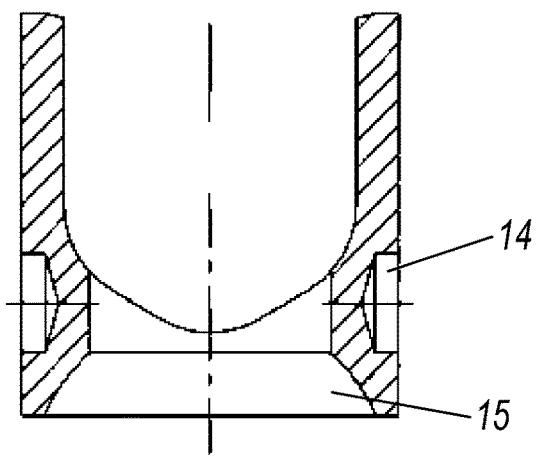
FIG. 7 is a front view of a press block of the present invention.
Figure 8:
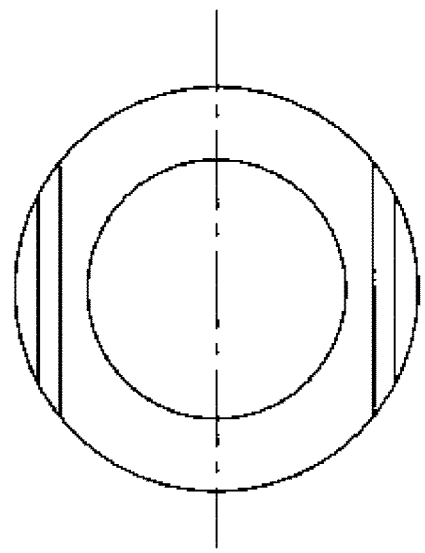
FIG. 8 is a top view of the press block.
Figure 9:
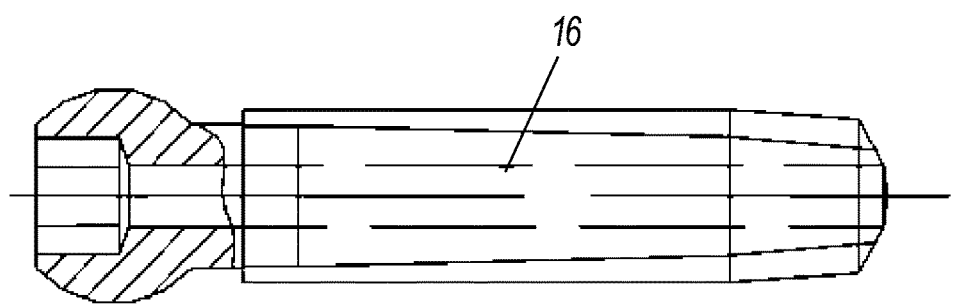
FIG. 9 is a schematic view of a pin with a hollow ball head of the present invention.

As shown in FIGS. 6 and 7, at least one pair of a first positioning groove 12 may be symmetrically arranged on the outer wall of the lengthened arm connector 3. The press block 4 is provided with a second positioning groove 14. The second positioning groove 14 and the first positioning groove 12 are co-axially arranged such that the pin 5 can be fixed to the end of the lengthened arm connector 3 when an external force is applied and the first positioning groove 12 and the second positioning groove 14 are thus passed through.

The head of the pin 5 is spherical, and a hexagon socket is disposed inside the head. The interior of the pin body of the pin 5 has a through hole, and the outer wall of the pin body is provided with a thread. The pin 5 can be locked within the range of motion via the press block 4.

In order to be capable of breaking the excess portion of the lengthened arm connector 3 off at the time of surgery, the outer wall and/or the inner wall of the lengthened arm connector 3 is(are) configured to have a groove(s). The groove is disposed on the middle-upper part of the internal thread 9. When both the outer wall and the inner wall of the lengthened arm connector 3 have the grooves, the grooves on the outer and inner walls are co-axially arranged. As shown in FIG. 6, the groove on the outer wall is configured to be a V-shaped groove 11, and the groove on the inner wall is configured to be a U-shaped groove 10.

The end of the lengthened arm connector 3 connecting to the pin may be a first spherical surface 13 (as shown in FIG. 6). The end of the press block 4 may be a second spherical surface 15 (as shown in FIG. 7). The first spherical surface 13 is configured to match the second spherical surface 15.

When the minimally invasive screw with double threaded plugs is tightened by two steps, the protrusion of the inner threaded plug cannot be directly exposed from the bottom of the outer threaded plug. If the protrusion is exposed by more than 1 mm, the pin body and the connecting rod can be locked simultaneously by only one step, which is not capable of making the vertebral body be distracted and pressurized effectively.

When conducting a surgery, firstly, the outer threaded plug 2 is tightened. At this time, the inner threaded plug 1 is in its loosened state. The pin body of the pin 5 can be locked within the range of motion by applying an external force on the press block 4. At this time, the connecting rod 17 is still movable in the axial direction. The inner threaded plug 1 is tightened to make the protrusion 7 engage with the connecting rod 17 and to make the connecting rod 17 be locked on the lengthened arm connector 3, thus preventing the vertebral body from rotating and loss of intervertebral height when the vertebral body is distracted and pressurized.

The minimally invasive screw with double threaded plugs of the invention is simple in structure and can avoid rotation of the vertebral body and loss of intervertebral height effectively when the vertebral body is distracted and pressurized so as to reduce operational difficulty for the operator and shorten operation time and thus improve surgical efficiency.

Preferred embodiments of the invention are described above. It should be noted that, for those skilled in the art, improvements and embellishments can be made without departing from the spirit and scope of the invention, and these improvements and embellishments should be considered within the scope of the invention.

REFERENCE LIST

1 Inner threaded plug
2 Outer threaded plug
3 Lengthened arm connector
4 Press block
5 Pin with a hollow ball head 6 Mounting groove
7 Protrusion
8 Opening
9 Internal thread
10 U-shaped groove
11 V-shaped groove
12 First positioning groove
13 First spherical surface
14 Second positioning groove
15 Second spherical surface
16 Through hole
17 Connecting rod

What is claimed is:

1. A minimally invasive screw with double threaded plugs, connecting to a connecting rod, comprising:
an inner threaded plug,
an outer threaded plug,
a lengthened arm connector including an inner wall, an outer wall, and an end,
a press block and
a pin with a hollow ball head,
wherein, the lengthened arm connector has a hollow interior, the connecting rod is configured to pass transversely through the lengthened arm connector, the outer threaded plug is movably disposed inside the lengthened arm connector, the inner threaded plug is movably disposed inside the outer threaded plug and is tightened relative to the outer threaded plug to make the connecting rod be fixed on the lengthened arm connector, and the press block is disposed on the inner wall of the lengthened arm connector to make the pin be fixed to the end of the lengthened arm connector to make the pin be locked within the range of motion when the outer threaded plug is tightened relative to the lengthened arm connector and thereby contacts and applies an external force on the press block;
wherein a lower part of the inner threaded plug has a protrusion for engaging with the connecting rod, to lock the connecting rod in the lengthened arm connector, and wherein the inner threaded plug and the outer threaded plug are configured to be independently tightened in two steps to lock the pin in position and to independently lock the connecting rod in position;
wherein at least one pair of a first positioning groove is symmetrically arranged on the outer wall of the lengthened arm connector, the press block is provided with a second positioning groove, the second positioning groove and the first positioning groove are co-axially arranged such that the pin can be fixed to the end of the lengthened arm connector when an external force is applied and the first positioning groove and the second positioning groove are thus passed through.

2. The minimally invasive screw with double threaded plugs of claim 1, wherein an upper part of the inner threaded plug is provided with a mounting groove for withstanding an external force to make the inner threaded plug rotate inside the outer threaded plug.

3. The minimally invasive screw with double threaded plugs of claim 2, wherein the mounting groove is a hexagon socket.

4. The minimally invasive screw with double threaded plugs of claim 1, wherein the outer threaded plug is provided with at least one opening for withstanding an external force to cause the outer threaded plug to rotate within the lengthened arm connector.

5. The minimally invasive screw with double threaded plugs of claim 4, wherein three openings are provided such that forces applied on the outer threaded plug are uniform while the inner threaded plug is rotating within the outer threaded plug.

6. The minimally invasive screw with double threaded plugs of claim 1, wherein at least one of the outer wall and the inner wall of the lengthened arm connector includes a groove for breaking the lengthened arm connector off in surgery.

7. The minimally invasive screw with double threaded plugs of claim 6, wherein the groove is disposed on a middle-upper part of an internal thread of the lengthened arm connector.

8. The minimally invasive screw with double threaded plugs of claim 1, wherein the outer wall and the inner wall of the lengthened arm connector include corresponding grooves, which are co-axially arranged, for breaking the lengthened arm connector off in surgery.

9. The minimally invasive screw with double threaded plugs of claim 1, wherein an interior of the pin with the hollow ball head has a through hole.

10. The minimally invasive screw with double threaded plugs of claim 8, wherein the grooves are disposed on a middle-upper part of the lengthened arm connector.

* * * * *